United States Patent [19]

Onishi et al.

[11] Patent Number: 4,920,109

[45] Date of Patent: * Apr. 24, 1990

[54] ANTIFUNGAL COMPOSITIONS AND METHOD OF CONTROLLING MYCOTIC INFECTIONS

[75] Inventors: Janet C. Onishi, Mountainside; Arthur A. Patchett, Westfield, both of N.J.

[73] Assignee: Merck & Co., Inc., Rahway, N.J.

[*] Notice: The portion of the term of this patent subsequent to May 1, 2007 has been disclaimed.

[21] Appl. No.: 182,615

[22] Filed: Apr. 18, 1988

[51] Int. Cl.[5] .................. A61K 31/58; A61K 31/335; A61K 31/35
[52] U.S. Cl. ................... 514/171; 514/449; 514/460; 514/467
[58] Field of Search ............... 514/171, 449, 460, 467

[56] References Cited

U.S. PATENT DOCUMENTS 4,806,565  2/1989  Hensens et al. .................. 514/467

FOREIGN PATENT DOCUMENTS 086092  8/1983  European Pat. Off. .

OTHER PUBLICATIONS

Chemical Abstracts; vol. 85 (1976); #187178k; Kabara et al.
Chemical Abstracts; vol. 94 (1981); #101307b; Monaghan et al.
J. Chem. Soc. (C), 1971, (23), pp. 3888–3891; Aldridge et al.
J. Chem. Soc. (D), 1970 (11), p. 639; Aldridge et al.
Ansehn, S et al., Scand. J. Infect. Dis., Suppl. 9, 62–66 ('76), Lew M. A. et al., J. Infect. Dis. 136, 263–270 (1977).
Medoff, G., et al., Proc. Nat. Acad. Sci. 69, 196–199 (1972).
Oehlschlager, A. C., et al., Biochem. 23, 3582–3589 (1984).
Gordee, R. S., et al., J. Antibiotics, 28, 112 (1975).
Rahier, A., et al., J. Biol. Chem. 259, No. 24, 15215 (1984).

Primary Examiner—Joseph A. Lipovsky
Attorney, Agent, or Firm—Alice O. Robertson; Joseph F. DiPrima

[57] ABSTRACT

Method of potentiating antifungal agents with 25-azasterol compound to produce superior antifungal compositions and use of the compositions to control mycotic infections is disclosed.

20 Claims, No Drawings

ANTIFUNGAL COMPOSITIONS AND METHOD OF CONTROLLING MYCOTIC INFECTIONS

BACKGROUND OF THE INVENTION

Systemic fungal infections caused by Candida species, *Cryptococcus neoformans, Histoplasma capsulatum* and the like are often serious or fatal. There continues to be a need for an antifungal agent which is effective and at the same time non-toxic to the patient being treated. A number of known antifungal agents while effective in eliminating the disease are of limited usefulness because of toxic or other undesirable side reactions. In many cases the toxicity is related to the amount of the drug and could be eliminated or reduced if a lesser amount of the drug could be employed. Thus, it would be desirable if a combination could be found which is synergistic or which has a second component that has a potentiating effect on the known antifungal agent thereby reducing the amount of drug required with concomitant reduction or elimination of side reactions.

There are reports in the literature that by administering amphotericin with other antibiotics, *Candida albicans* is sensitized to antifungal agents. Thus, for example, minocycline and amphotericin B have been found to be a synergistic composition against *Candida albicans*, Leev et al, Brit. J. Infect. Dis., 136, 263–270 (1977). However, combinations with amphotericin is not satisfactory because of the toxicity of amphotericin to human beings.

STATEMENT OF THE INVENTION

The present invention concerns improved compositions and methods useful for the control of fungi and particularly for the treatment of mycotic infections made possible by the discovery that when certain azasterol compounds are employed in combination with certain fungistatic compounds, there is potentiation in the activity of these compounds resulting in superior antifungal combinations and in some cases resulting in useful fungicidal combinations. Some azasterols may show some antifungal properties in which case the potentiated compositions may be considered a synergistic composition.

DESCRIPTION OF THE INVENTION

According to the present invention it has been discovered that the antifungal properties of an antifungal agent may be potentiated by coadministering a 25-azasterol compound with the antifungal agent. Thus, when a 25-azasterol compound, at a concentration not inhibitory to the growth of fungi is employed with a subfungistatic amount of an antifungal agent, the sensitivity of fungal organisms to the antifungal agents is unexpectedly significantly increased providing a synergistic antifungal composition. It has further been discovered that with certain fungistats the combinations have resulted unexpectedly in fungicidal compositions.

In view of the effectiveness of the combination against fungi causing mycotic infections, the present invention is further directed to methods and compositions for combatting fungi causing mycotic infections comprising treating the infected site with an antifungally effective amount of a composition comprising a subfungistatic amount of an antifungal compound and a 25-azasterol compound in an amount not inhibitory to fungal growth. The invention is further directed to a method for treating mycotic infections comprising administering to a subject in need of such treatment, an antifungally effective amount of a composition comprising a subfungistatic amount of an antifungal compound and an amount of 25-azasterol not inhibitory to fungal growth.

Fungistats which have been potentiated most effectively and indeed unexpectedly to give rise to fungicidal compositions are those fungistats which act on the enzymes in the biochemical pathway prior to the formation of lanosterol. Inhibitors of enzymes in the mevalonic acid synthesis such as HMG-CoA synthase, $\beta$-ketothiolase ($\beta$-ketoacyl-coenzyme A thiolase) and HMG-CoA reductase as well as those which inhibit enzymes which act at later stages in the pathway to lanosterol including squalane epoxidase are particularly important in the formation of novel fungicidal compositions. Since all of these enzymes are enzymes in the pathway of lanosterol synthesis, the antifungal agents which act on these enzymes when spoken of in general terms will be referred to as lanosterol synthesis inhibitors. In view of the effectiveness of 25-azasterols on potentiating the fungistats which are lanosterol synthesis inhibitors, the invention is further directed to methods and compositions for treating mycotic infections comprising a subfungistatic amount of a lanosterol synthesis inhibitor and a 25-azasterol compound in an amount non-inhibitory to fungal growth.

Although mycotic infections may be alleviated by fungistatic compositions, there is no cure except with fungicidal compositions. A very special aspect of the present invention are new fungicidal compositions comprising a 25-azasterol compound and a HMG-CoA synthase inhibitor, or a $\beta$-ketothiolase inhibitor, or a HMG-CoA reductase inhibitor or a squalene epoxidase inhibitor.

The "25-azasterol compound" useful in the improved antifungal compositions and methods of the present invention are characterized by a hydroxyl group or an esterified hydroxyl group in the 3-position, an unsaturation in Ring B and a nitrogen at the 25 position in the side chain of the steroid ring system as may be seen from the following formula (I):

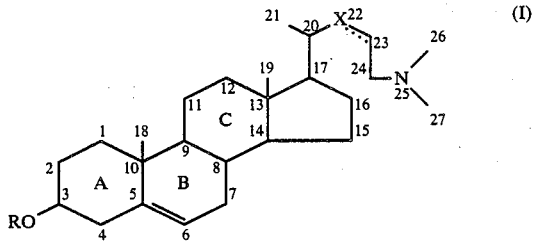

wherein R is hydrogen or lower acyl, X is CH, $CH_2$ or O; and the ......... on the side chain indicates that the bond may be a single or a double bond provided that when X is O, or $CH_2$, it is a single bond.

Except as hereinafter indicated, the azasterol compounds are compounds available or reported in the literature or are ester derivatives of known compounds readily prepared by conventional esterification methods. The following are representative examples of specific 25-azasterols which are particularly useful in the present invention:

(a) 25-azacholesterol; 17$\beta$-[[3-(dimethylamino)-propyl]-methylamino]androst-5-en-3$\beta$-ol

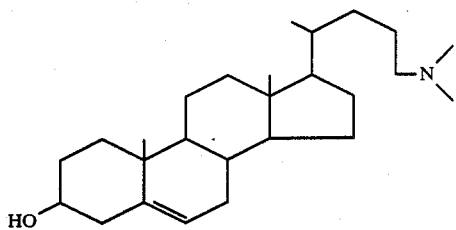

(b) N,N-dimethyl-3β-hydroxy-5,22(Z)choladiene-24-amine; (3β-22Z)-24-(dimethylamino)chola-5,22-diene-3-ol

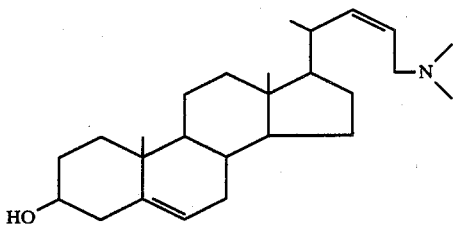

The foregoing may be prepared by the Wittig reaction on an i-steroid carboxaldehyde, followed by rearrangement and hydrolysis as described in copending application U.S. Ser. No. 169,669 in the name of N. G. Steinberg, now abandoned.

(c) N,N-dimethyl-3β-acetoxy-5,22(Z)choladiene-24-amine; (3β,22Z)-24-(dimethylamino)chola-5,22-dien-3-ol acetate.

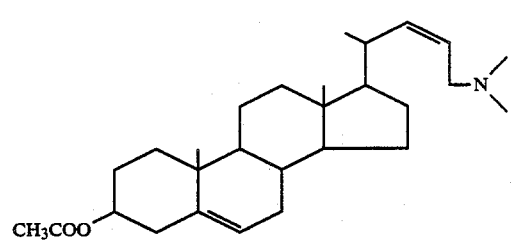

The preparation of the acetate is also the subject of U.S. Ser. No. 169,669 in the name of N. G. Steinberg, now abandoned.

(d) 25-aza-22-oxacholesterol; (3,20)-20-[2-(dimethylamino)ethoxy]pregn-5-en-3-ol

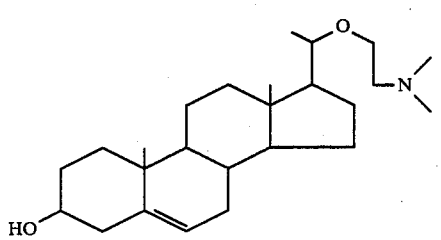

The preferred 25-azasterol compound is 25-azacholesterol (Compound Ia).

The antifungal compounds which may be potentiated by the 25-azasterol compounds are diverse in structure but are useful especially against organisms causing mycotic infections. A number of the suitable antifungal compounds are those known to be inhibitors of enzymes in the biochemical pathway to lanosterol. However, a number of antifungal agents which are not inhibitors of enzymes in the biochemical pathway to lanosterol or where mode of antifungal action is not established but which are known or can be shown to possess antifungal properties have also been found to be potentiated and to form useful synergistic antifungal compositions. These compounds of diverse structure which are the main antifungal component in the methods and compositions of the present invention are non-steroidal in nature, although as previously noted, some of since the 25-azasterol compounds have some antifungal properties. Representative of the compounds which are potentiated by the 25-azasterol compound include a number of new fungistats as well as established fungistats recognizable by USAN or generic names. The following representative compounds illustrate the diverse nature of the antifungal agents which may be potentiated but are not to be construed as being limited thereto.

(1) 11-(3-hydroxymethyl-4-oxo-2-oxetanyl)-7-methyl-2,4-undecadienoic acid. (Compound A)

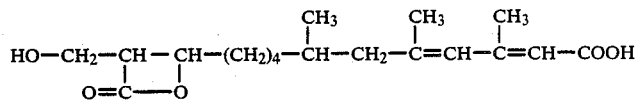

This compound is reported in J. Chem. Soc. (c), 1971, 3888; the antifungal properties is the subject of U.S. Ser. No. 825,496, filed Feb. 3, 1986, now abandoned and the HMG-CoA synthase inhibitor property, the subject of U.S. Ser. No. 21,848, filed Mar. 4, 1987, now U.S. Pat. No. 4,847,271, Jul. 11, 1989.

(2) 5-(1-hydroxy-2,4,6-heptatriynyl)-2-oxo-1,3-dioxolane-4-heptanoic acid. (Compound B)

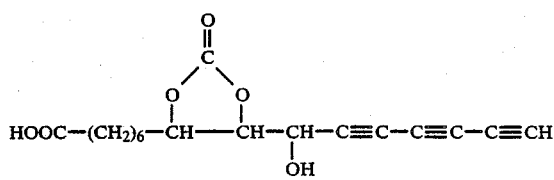

The compound may be prepared by the cultivation of microorganism ATCC 53,614, 53,615 or 53,616 followed by isolation as described together with antifungal properties in U.S. Ser. No. 53,920, filed May 26, 1987, now U.S. Pat. No. 4,806,565, Feb. 21, 1989. The β-ketothiolase activity is subject of U.S. Ser. No. 53,973, filed May 26, 1987, now U.S. Pat. No. 4,780,311.

(3) 1-methyl-2-nonyl-5-(phenylmethyl)-3-pyrrolidinol (Compound C)

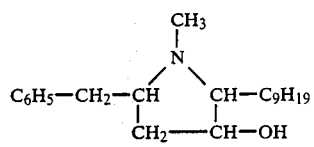

The compound may be prepared by the cultivation of microorganism ATCC 22947 followed by isolation as described together with antifungal properties in copending application U.S. Ser. No. 172,164, filed in the name of R. E. Schwartz et al., now U.S. Pat. No. 4,847,284, Jul. 11, 1989.

(4) (E)-N-(6,6-dimethyl-2-hepten-4-ynyl)-N-methyl-1-naphthalenemethylamine; terbinafine (Compound D)

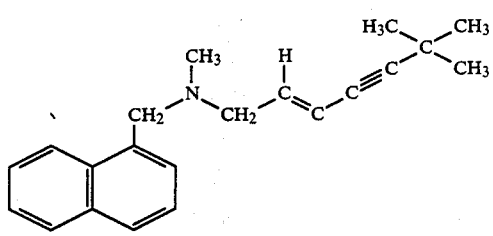

(5) 1,2,3,7,8,8a-hexahydro-3,7-dimethyl-8-[2-(tetrahydro-4-hydroxy-6-oxo-2H-pyran-2-yl)ethyl]-1-naphthalenyl-2-methyl butanoate; lovastatin (Compound E)

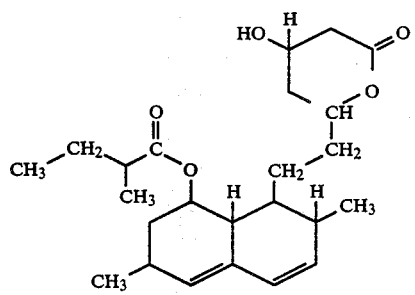

(6) 1-ethyl-1,4-dihydro-7-methyl-4-oxo-1,8-naphthyridine-3-carboxylic acid; nalidixic acid (Compound F)

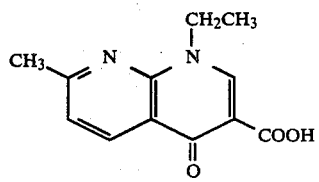

(7) 5-chloro-6-(7,8-epoxy-10-hydroxy-2-oxo-3,5-undecadienyl)-β-resorcyclic acid μ-lactone; monorden (Compound G)

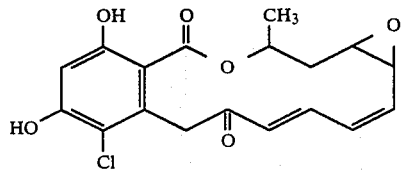

(8) 2-(4-thiazolyl)-1H-benzimidazole; thiabendazole (Compound H)

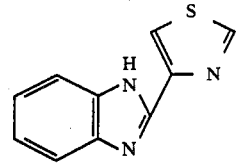

(9) 4-[2-(3,5-dimethyl-2-oxocyclohexyl)-2-hydroxyethyl]2,6-piperidinedione; cycloheximide (Compound J)

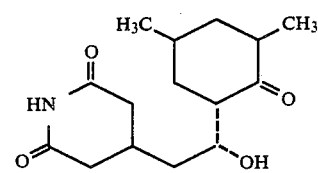

(10) 4,7-bis(dimethylamino)-1,4,4a,5,5a,6,11,12a-actahydro-3,10,12,12a-tetrahydroxy-1-dioxo-2-naphthacenecarboxamide; minocycline (Compound K)

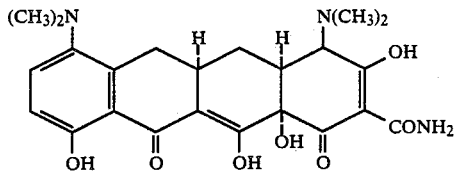

(11) 4-(dimethylamino)-1,4,4a,5,5a,6,11,12a-octahydro-3,6,10,12,12a-pentahydroxy-6-methyl-1,11-dioxo-2-naphthacenecarboxamide; tetracycline (Compound L)

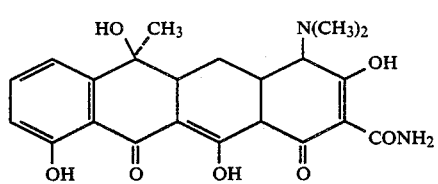

(12) N-methyl-N-(3-phenyl-2-propenyl)-1-naphthalenemethanamine; naftifine (Compound M)

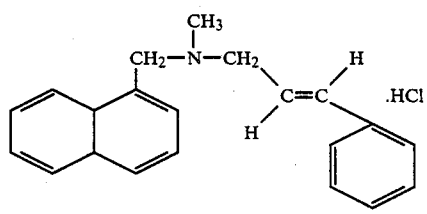

(13) 2-(p-methoxybenzyl)-3,4-pyrrolidinediol-3-acetate; anisomycin (Compound N)

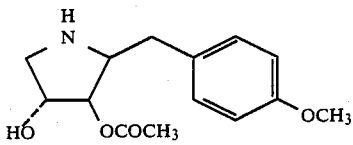

The foregoin compounds hereinafter may be identified by the generic or USAN name or by "Compound" followed by the letter designations.

As previously indicated, the combinations which are noteworthy are those combinations of 25-azasterol compounds with inhibitors of enzymes in the biochemical pathway in lanosterol synthesis. These combinations show fungicidal properties as well as synergistic antifungal properties. Especially noteworthy are combinations of 25-azasterol compounds with inhibitors of mevalonic acid synthesis, i.e., a 25-azasterol compound with a HMG-CoA synthase inhibitor compound; a 25-azasterol compound with a β-ketothiolase inhibitor compound and a 25-azasterol compound with a HMG-CoA reductase inhibitor compound. Particularly useful specific combinations are 25-azacholesterol as the 25-azasterol compound with 11-(3-(hydroxymethyl)-4-oxo-2-oxetanyl)-7-methyl-2,4-undecadienoic acid as (Compound A) the HMG-CoA synthase inhibitor compound, with 5-(1-hydroxy-2,4,6-heptatriynyl)-2-oxo-b 1,3-dioxalane-4-heptanoic acid (Compound B) as the β-ketothiolase inhibitor compound, and with 1,2,3,7,8,8a-hexahydro-3,7-dimethyl 8-[2-(tetrahydro-4-hydroxy-6-oxo-2H-pyran-2-yl)ethyl]-1-naphthalenyl-2-butanoate (Compound E; lovastatin) as the HMG-CoA reductase inhibitor compound. Also noteworthy are combinations of 25-azasterol compounds with squalene epoxidase inhibitor compounds such as (E)-N-(6,6-dimethyl-2-hepten-4-ynyl)-N-methyl-1-naphthalene-methylamine (Compound D; terbinafine) and N-methyl-N-(3 phenyl-2-propenyl)-1-naphthalenemethanamine hydrochloride (Compound M; naftifine). Especially useful of the latter is the combination of 25-azacholesterol and terbinafine.

The synergistic antifungal and fungicidal combinations of the present invention are effective in the treatment of mycotic infections caused by such fungal organisms as those of the Candida species, for example, *C. albicans, C. parapsilosis, C. tropicalis, C. pseudotropicalis, C. krusei, C. rugosa, C. quilliermondii, C. stellatoidea*; those of the *Aspergillus* species such as *A. fumigatus*; and other disease-causing fungi such as *Cryptococcus neoformans; Torulopsis glabrata; Rhizopus rhizopodiformis; Coccidioides immitis; Sporothrix schenkii; Histoplasma capsulatum*; and *Blastomyces dermatitidis.*

The method for potentiating the antifungal effectiveness of an antifungal compound comprising employing a subfungistatic amount of an antifungal compound together with a 25-azasterol compound which if it has some fungistatic property is employed at a concentration not inhibitory to the growth of fungi. The potentiated combination may then be employed to control fungal growth by administering to or directing to a site where control of fungi is desired, an antifungally effective amount of a composition comprising a 25-azasterol compound in an amount non-inhibitory to fungal growth and an antifungal compound. Alternatively, each compound may be administered sequentially. The method is particularly directed to treating subjects with mycotic infections to control fungal growth and the disease caused by fungi by comprising administering to said subjects an antifungally effective amount of a composition comprising a 25-azasterol compound together with an antifungal agent. The application may be made at a site remote from that of the infection such as would be the case with oral or parenteral administration, or directly at the site infected with fungi. The agents may be administered with or without, preferably with, a pharmaceutically acceptable carrier in the amounts hereinafter set forth. By the administration of the amounts of the agents as hereinafter set forth, a potentiated or synergistic fungistatic interaction of the drugs is achieved which is wholly unexpected.

With some combinations, namely, azasterols with lanosterol synthesis inhibitors, a fungicidal effect also may be achieved, usually at higher concentrations. With combinations which have a fungicidal effect, the invention is directed to killing fungi by administering to the site infected with fungi, the fungicidal combination. It is further directed to treating subjects with mycotic infection to eradicate, the disease-causing fungi by administering a fungicidal composition comprising an azasterol compound and a HMG-CoA synthase inhibitor, an azasterol compound and a β-ketothiolase inhibitor an azasterol compound and a HMG-CoA reductase inhibitor or an azasterol compound and a squalene epoxidase inhibitor. As with fungistatic compositions, the application may be made at a site remote from the infection as in oral or parentaral administration, or may be made directly at the site of infection. The administration may be made with or without a carrier and in amounts as hereinafter detailed. By these operations, a wholly unexpected eradication of fungi has been achieved.

The effectiveness of the combination generally depends on the original susceptibility of the particular organism or strain of organism to the fungistat to be employed in combination with the azasterol compound. Thus, although the azasterol compound has a potentiating effect on fungistats generally, the apparent greater effect of particular combinations may depend on the original susceptibility of the organism to the unmodified fungistat. In the case of fungistats which are known to be lanosterol synthesis inhibitors, it has been found with these fungistats that not only a synergistic fungistatic combination is obtained but also a fungicidal combination is obtained.

The potentiation of the antifungal properties of an antifungal agent by coadministering a 25-azasterol compound and the production of a synergistic antifungal as well as in many instances of a fungicidal effect may be illustrated by the in vitro interaction studies for the determination of activity. In these tests against representative fungal organisms known to be the causative agent of mycotic infections, including *Candida albicans*, other Candida species, and a number of other fungi, synergistic antifungal properties have been demonstrated with a 25-azasterol compound together with various fungistatic lanosterol synthesis inhibitor compounds.

Representative antifungal properties of the combination of a 25-azasterol compound and an antifungal agent may be seen in the following examples, which are deemed to be representative but which are not to be construed as limiting.

EXAMPLE I

Potentiation of Anti-Candida Activity by 25-Azacholesterols

Using standard a disk diffusion assay in which the agar was supplemented with 25-azacholesterol, and using two strains of Candida albicans, MY 992 and MY 1055, drugs were tested to determine the extent of potentiating effect of the 25-azacholesterol on the antifungal properties of the drugs. Representative potentiating effect of 25-azacholesterol on the anti-Candida activity of some antifungal agents may be seen from the following table:

TABLE I

| Antifungal Drug | μg/disk | Zone diameters (mm) | | | | | |
|---|---|---|---|---|---|---|---|
| | | MY 992 | | | MY 1055 | | |
| | | 25-Azacholesterol | | | | | |
| | | μg/ml | | | μg/ml | | |
| | | 0 | 20* | Δ | 0 | 20* | Δ |
| Nalidixic acid | 50 | 0 | 25 | 25 | 15 | 25 | 10 |
| | 10 | 0 | 16 | 16 | 0 | 15 | 15 |
| Lovastatin | 50 | 17 | 25 | 8 | 17 | 25 | 8 |
| | 10 | 12 | 18 | 6 | 12 | 20 | 8 |
| Terbinafine | 50 | 19 | 30 | 14 | 17 | 31 | 14 |
| | 10 | 15 | 24 | 11 | 15 | 27 | 12 |
| Compound C | 5 | 0 | 34 | 31 | 0 | 40 | 40 |
| | 0.5 | 0 | 30 | 30 | 0 | 35 | 35 |
| Nikkomycin | 50 | 0 | 18 | 18 | 0 | 16 | 16 |
| | 10 | 0 | 0 | 0 | 0 | 0 | 0 |
| Monorden | 50 | 15 | 22 | 7 | 15 | 18 | 3 |
| | 10 | 0 | 20 | 20 | 0 | 17 | 17 |
| Thiabendazole | 50 | 0 | 20 | 20 | 0 | 20 | 20 |
| | 10 | 0 | 17 | 17 | 0 | 18 | 18 |
| Cycloheximide | 50 | 0 | 17 | 17 | 0 | 15 | 15* |
| Minocycline | 50 | 14 | 25 | 11 | 15 | 20 | −5 |
| Tetracycline | 50 | 0 | 13 | 13 | 0 | 0 | 0 |

*At 20 μg/ml, 25-azacholesterol alone did not inhibit the growth of C. albicans MY 992 or MY 1055.

EXAMPLE II

Sabouraud dextrose agar was inoculated with Candida albicans MY 992 to $1 \times 10^4$ colony forming units/milliliter (cfu/ml). The azasterols, 25-azacholesterol (Compound Ia) and 25-aza-22-oxacholesterol (Compound Id), dissolved in ethanol:Brij 58 (1:1 v/v), were added in a volume equivalent to 10 μl/ml. Assay plates were poured. Sensitivity disks prepared to provide stated concentrations of the drug were placed on the plates. The plates were incubated for 17 hours at 37° C. At the end of this period, zones of inhibition were measured. The effect of the azasterols in increasing the sensitivity of the organism to the drug may be seen in Table II.

TABLE II

| Drug | μg/disk | Zone of Inhibition against C. albicans MY 992 | | |
|---|---|---|---|---|
| | | Control | Compound Ia | Compound Id |
| Anisomycin | 50 | 0 | 15 | 14 |
| Cycloheximide | 50 | 0 | 16 | 14 |
| Nalidixic acid | 50 | 0 | 25 | 20 |
| Nikkomycin | 50 | 0 | 30 | 31 |
| Tetracycline | 50 | 0 | 16 | 15 |
| Lovastatin | 50 | 13 | 21 | 18 |
| " | 5 | 0 | 15 | 15 |
| Naftifine | 50 | 0 | 20 | 20 |
| " | 5 | 0 | 12 | 12 |
| Terbinafine | 50 | 17 | 25 | 25 |
| " | 5 | 12 | 19 | 20 |

EXAMPLE III

A disk diffusion assay was carried out in which several azasterol compounds were employed with several antifungal agents to determine the potentiating properties of the azasterol compounds.

The azasterols were titrated in Sabouraud dextrose agar which was inoculated with C. albicans MY992. Sensitivity disks containing antifungal agent at 50 μg/disk were applied to the plates. The plates were incubated at 37° C. for 18 hours. At the end of this period the plates were read for zones of inhibition.

The results of azasterol compounds: 25-azacholesterol (Compound Ia), N,N-dimethyl-3β-acetoxy-5,22(Z)-choladiene-24-amine (Compound Ic) and N,N-dimethyl-3β-hydroxy-5,22(Z)-choladiene-24-amine (Compound Ib) with antifungal agents: cycloheximide; nalidixic acid and terbinafine are seen in Table III. (Compound Ic inhibited growth at 25 μg/ml when employed along.)

TABLE III

| Azasterol Compound | μg/ml | Cycloheximide 50 μg/disk | Nalidixic acid 50 μg/disk | Terbinafine 50 μg/disk |
|---|---|---|---|---|
| Control | | 0 | 0 | 17 |
| Compound Ia | 25 | 16 h | 27 | 26 |
| | 6.25 | 14 h | 25 | 24 |
| | 1.56 | 13 h | 22 | 25 |
| | 0.39 | 0 | 21 | 24 |
| Compound Ic | 25 | Inhibited growth | | |
| | 6.25 | 14 h | 19 | 16 |
| | 1.56 | 0 | 15 | 18 |
| | 0.39 | 0 | 11 | 18 |
| Compound Ib | 25 | 15 h | 36 | 29 |
| | 6.25 | 15 h | 35 | 26 |
| | 1.56 | 0 | 23 | 21 |
| | 0.39 | 0 | 18 | 22 |

EXAMPLE IV

A. Synergistic Effect

Minimum inhibitory concentration (MIC) of nalidixic acid, nikkomycin, lovastatin and terbinafine alone and in combination with 25-azacholesterol were determined.

Synthetic Medium (SM, Difco yeast nitrogen base supplemented with 0.5 percent dextrose) and complex Medium (CM, Difco Sabouraud dextrose agar) were inoculated with $1 \times 10^4$ cfu/ml (colony forming units per milliliter) of exponential phase Candida albicans MY 992. Dilution tubes containing 10 μl/ml of dimethyl sulfoxide (DMSO) and 10 ul/ml of ethanol-Brij 58 (1:1, v/v) were prepared. The test drugs were titrated from 400 to 1.56 μg/ml. The tubes were incubated for 17 hours at 37° C., read and the minimum inhibitory concentrations determined. The MIC was taken as the minimum concentration which prevented visible growth. The results are seen in Table IVA.

TABLE IVA

| Drug | Medium | Minimum Inhibitory Concentration (MIC) of Drug μg/ml Concn of 25-Azacholesterol (μg/ml) | | |
|---|---|---|---|---|
| | | 0 | 1.25 | 12.5 |
| Nalidixic Acid | SM | 200 | 100 | 100 |
| | CM | >400 | 100 | 100 |
| Nikkomycin | SM | >400 | 50 | 50 |
| | CM | >400 | 200 | 200 |
| Lovastatin | SM | 400 | 100 | 50 |
| | CM | 200 | 100 | 50 |
| Terbinafine | SM | 200 | 50 | 25 |
| | CM | 200 | 25 | 25 |

B. Fungicidal Effect

The fungicidal effect of the drugs alone and in combination with 25-azacholesterol were determined by diluting the titration tubes which had been used to determine the minimum inhibitory concentrations.

The test samples were diluted by 10-fold increments in microtiter dishes. A 5 microliter aliquot of each dilution was stamped on Sabouraud dextrose agar and the plates incubated for 24 hours at 37° C. The presence of viable cells in the MIC tubes was noted and the minimum fungicidal concentration (MFC) determined. The results are seen in Table IVB.

TABLE IVB

| Drug | Minimum Fungicidal Concentration (MFC) of Drug μg/ml Concn of 25-Azacholesterol (μg/ml) | |
|---|---|---|
| | 0 | 12.5 |
| Nalidixic Acid | >400 | >400 |
| Nikkomycin | >400 | >400 |
| Lovastatin | >400 | 100 |
| Terbinafine | 400 | 25 |

EXAMPLE V

The potentiating effect of 25-azacholesterol on the minimal inhibitory concentration (MIC) or minimal fungicidal concentration (MFC) of certain antifungal agents against *C. albicans* MY 1055 are seen in the following experiments.

*C. albicans* MY 1055 was grown overnight in Difco yeast nitrogen base supplemented with 0.5 percent glucose at 37° C. The culture was diluted into fresh medium to $1 \times 10^4$ cfu/ml. A one-milliliter aliquot was added to tubes containing drugs serially diluted by four-fold increments. The 25-azacholesterol was used as the dihydrochloride salt. After inoculation, the tubes were incubated for 24 hours at 37° C. at 300 rpm. The MIC was determined as the lowest concentration preventing visible growth.

The minimum fungal concentration (MFC) was determined by diluting the drug-treated overnight cultures by 10-fold increments in microtiter dishes. Five microliters of each dilution was stamped on Sabouraud dextrose agar. The plates were incubated for 24 hours at 37° C. and observed for growth. The MFC was determined as the lowest concentration to kill which was greater than or equal to 2 logs of the initial colony forming units.

The results are seen in Table V.

TABLE V

| Drug | Minimum Inhibitory Concn μg/ml | | Fungicidal Concn μg/ml | |
|---|---|---|---|---|
| | 25-Azacholesterol μg/ml | | | |
| | 0 | 25 | 0 | 25 |
| Nalidixic Acid | 400 | 100 | 400 | 400 |
| Lovastatin | 25 | 1.56 | 100 | 25 |
| Terbinafine | 100 | 1.56 | 400 | 25 |
| Compound C | 400 | 25 | >400 | >100 |
| Nikkomycin | 100 | 100 | 400 | >100 |
| Monorden | 25 | 6.25 | 100 | 100 |
| Minocycline | >400 | 400 | >400 | 400 |

EXAMPLE VI

In operations carried out in the manner described in Example V, minimum inhibitory concentration and minimum fungicidal concentrations of the combinations of 25-azacholesterol with 5-(1-hydroxy-2,46-heptatriynyl)-2-oxo-1,3-dioxalane-4-heptanoic acid carbonate salt (Compound B) and with 11-(3-(hydroxymethyl)-4-oxo-2-oxetanyl)-7-methyl-2,4-undecadienoic acid (Compound A) against *Candida albicans* MY 1055 were determined. The results are seen in Table VI.

TABLE VI

| Drug | MIC μg/ml | | MFC μg/ml | |
|---|---|---|---|---|
| | 25-Azacholesterol (μg/ml) | | | |
| | 0 | 25 | 0 | 25 |
| Compound B | 1.25 | <0.31 | 5.0 | <0.31 |
| Compound A | 3.1 | <3.1 | 12.5 | <3.1 |

EXAMPLE VII

The enhanced activity of combinations against a wide spectrum of yeasts and filamentous fungi may be seen in the combinations of 25-azacholesterol with terbinafine, monorden, and compound c in an agar dilution assay. The method employed was as follows: 25-azacholesterol was solubilized in distilled water and concentrations in the range of from 1.28 to 0.00063 mg/ml were first prepared and then diluted in agar medium to obtain test concentrations of 128 to 0.063 mg/ml. Terbinafine, monorden and Compound c were solubilized in 10 percent dimethyl sulfoxide and thereafter diluted as with the 25-azacholesterol except that the maximum final concentration of Compound C was 64 μg/ml.

Each diluted drug was added to cooled, molten yeast nitrogen base plus glucose agar (1.0 ml of drug plus 9.0 ml agar). Appropriate solvent and media controls (drug free) also were prepared. Prepared plates were stored in the dark at room temperature overnight prior to use.

The yeast cultures, maintained in yeast maltose (YM) broth, were transferred to fresh YM medium and incubated overnight at 37° C. with shaking (250 rpm). After incubation, each culture was diluted in sterile saline to yield final concentrations of $3 \times 10^5$ to $3 \times 10^6$ colony forming units per milliliter (cfu/ml). The isolates of two species of Aspergillus and of Penicillium were maintained on potato dextrose agar slats and spore suspensions made folowing vigorous shaking with sterile glass beads. The spore preparations were used as the inocula for these three filamentous fungi.

Each prepared plate was inoculated with 21 yeast-like and filamentous fungi using a Denley Multipoint Inoculator (Denley, Sussex, England). The inoculator delivers approximately 0.001 ml to the agar surface resulting in inoculation of from $3 \times 10^2$ to $3 \times 10^3$ colony forming units. The plates were incubated at 28° C. for 48 hours. The minium inhibitory concentrations (MICs) were recorded as the lowest concentration of drug showing no growth or less than three cfus/spot.

Potentiation of activity by the azasterol compound was seen in all combinations against some of the organisms. Combinations with monorden, and terbinafine gave greatly increased activity against almost every organism tested.

The results with monorden, Compound C and terbinafine are seen in Tables VIIA, VIIB, and VIIC. In all combinations, tests were carried out in which 25-azacholesterol (AC) was maintained at 128 μg/ml. Monorden (M) or terbinafine (T) was titrated from 128 μg/ml to 0.063 μg/ml, which Compound C (Cpd C) was titrated from 64 μg/ml to 0.063 μg/ml. With terbinafine additional tests were carried out in which 25-azacholesterol was maintained at 32 μg/ml or 8 μg/ml while terbinafine was titrated from 128 82 g/ml to 0.063 μg/ml. The minimum inhibitory concentration in the combination column is that of the titrated fungistat in the mixture. In combinations with terbinafine no significant reduction in potentiating activity was observed by reducing 25-azacholesterol concentrations from 128 μg/ml to 8 μg/ml.

A similar test employing 25-azacholesterol with nalidixic acid showed similar but less potent potentiating effect. The pattern of activity was similar to that of the combination with monorden exhibiting high potentiation against *C. pseudotropicalis, C, krusei* and *Penicillium italicum*. However, unlike in the combination with monorden, 25-azacholesterol showed little potentiating effect on nalidixic acid against most strains of *Candida albicans*.

TABLE VIIA

| FUNGUS | | AC (alone) | M (with 128AC) | M (alone) |
|---|---|---|---|---|
| Cryptococcus neoformans | MY1051 | >128 | <0.063 | 16 |

MINIMUM INHIBITORY CONCENTRATION (μg/ml)

TABLE VIIA-continued

| FUNGUS | | AC (alone) | M (with 128AC) | M (alone) |
|---|---|---|---|---|
| Cr. neoformans | MY1146 | >128 | 0.5 | 16 |
| Candida albicans | MY1058 | >128 | 1 | 32 |
| C. albicans | MY1055 | >128 | 2 | 32 |
| C. albicans | MY0992 | >128 | 4 | 64 |
| C. albicans | MY1013 | >128 | 2 | 32 |
| C. albicans | MY1029 | >128 | 2 | 32 |
| C. parapsilosis | MY1009 | >128 | 2 | 64 |
| C. parapsilosis | MY1010 | >128 | 0.25 | 32 |
| C. tropicalis | MY1011 | >128 | 8 | >128 |
| C. tropicalis | MY1012 | >128 | 0.25 | 1 |
| C. pseudotropicalis | MY1040 | <0.063 | <0.063 | >128 |
| C. krusei | MY1020 | <0.063 | <0.063 | 64 |
| C. rugosa | MY1022 | >128 | 32 | >128 |
| C. quilliermondii | MY1019 | >128 | 4 | >128 |
| C. stellatoidea | MY1018 | >128 | 8 | >128 |
| Torulopsis glabrata | MY1059 | >128 | 16 | >128 |
| Sac. cerevisiae | MY1027 | >128 | 0.125 | 32 |
| Aspergillus fumigatus | MF4839 | >128 | 4 | 32 |
| A. flavus | MF0383 | >128 | 4 | 32 |
| Penicillium italicum | MF2819 | 1 | <0.063 | 16 |

TABLE VIIB

MINIMUM INHIBITORY CONCENTRATION (μg/ml)

| FUNGUS | | AC (alone) | Cpd C (with 128AC) | Cpd C (alone) |
|---|---|---|---|---|
| Cryptococcus neoformans | MY1051 | >128 | 4 | >64 |
| Cr. neoformans | MY1146 | >128 | 64 | >64 |
| Candida albicans | MY1058 | >128 | 2 | >64 |
| C. albicans | MY1055 | >128 | <0.063 | >64 |
| C. albicans | MY0992 | >128 | >64 | >64 |
| C. albicans | MY1013 | >128 | 1 | >64 |
| C. albicans | MY1029 | >128 | <0.063 | >64 |
| C. parapsilosis | MY1009 | >128 | 0.125 | >64 |
| C. parapsilosis | MY1010 | >128 | <0.063 | >64 |
| C. tropicalis | MY1011 | >128 | 16 | >64 |
| C. tropicalis | MY1012 | >128 | 32 | >64 |
| C. pseudotropicalis | MY1040 | <0.063 | <0.063 | 32 |
| C. krusei | MY1020 | <0.063 | <0.063 | >64 |
| C. rugosa | MY1022 | >128 | <0.063 | >64 |
| C. quilliermondii | MY1019 | >128 | <0.063 | >64 |
| C. stellatoidea | MY1018 | >128 | 16 | >64 |
| Torulopsis glabrata | MY1059 | >128 | >64 | >64 |
| Sac. cerevisiae | MY1027 | >128 | <0.0630 | 32 |
| Aspergillus fumigatus | MF4839 | >128 | >64 | >64 |
| A. flavus | MF0383 | >128 | >64 | >32 |
| Pencillium italicum | MF2819 | 1 | <0.063 | >64 |

TABLE VIIC

MINIMUM INHIBITORY CONCENTRATION (μg/ml)

| FUNGUS | | AC (alone) | T (with 128AC) | T (with 128AC) | T (with 32AC) | T (with 8AC) | T (alone) |
|---|---|---|---|---|---|---|---|
| Cryptococcus neoformans | MY1051 | >128 | 1 | 1 | 2 | 8 | |
| Cr. neoformans | MY1146 | >128 | 2 | 2 | 2 | 32 | |
| Candida albicans | MY1058 | >128 | 4 | 4 | 4 | 128 | |
| C. albicans | MY1055 | >128 | 4 | 4 | 4 | 128 | |
| C. albicans | MY0992 | >128 | >128 | >128 | >128 | >128 | |
| C. albicans | MY1013 | >128 | 4 | 4 | 4 | 64 | |
| C. albicans | MY1029 | >128 | 2 | 2 | 2 | 128 | |
| C. parapsilosis | MY1009 | >128 | 0.125 | <0.063 | 0.125 | 4 | |
| C. parapsilosis | MY1010 | >128 | 0.125 | <0.063 | 0.25 | 4 | |
| C. tropicalis | MY1011 | >128 | 16 | 16 | 16 | 128 | |
| C. tropicalis | MY1012 | >128 | 4 | 4 | 4 | 8 | |
| C. krusei | MY1020 | 0.5 | <0.063 | <0.063 | <0.063 | 64 | |
| C. rugosa | MY1022 | >128 | 4 | 4 | 4 | >128 | |
| C. quilliermondii | MY1019 | >128 | 1 | 0.5 | 1 | 32 | |
| C. stellatoidea | MY1018 | >128 | 8 | 8 | 8 | 64 | |
| Torulopsis glabrata | MY1059 | >128 | >128 | >128 | >128 | >128 | |
| Sac. cerevisiae | MY1027 | >128 | <0.063 | 16 | 32 | 128 | |
| Aspergillus fumigatus | MF4839 | >128 | 0.125 | 0.125 | <0.063 | 0.5 | |
| A. flavus | MF0383 | >128 | <0.063 | <0.063 | <0.063 | 0.5 | |

TABLE VIIC-continued

| | | MINIMUM INHIBITORY CONCENTRATION (μg/ml) | | | | |
|---|---|---|---|---|---|---|
| FUNGUS | AC (alone) | AC (with 128AC) | T (with 128AC) | T (with 32AC) | T (with 8AC) | T (alone) |
| *Penicillium italicum* MF2819 | >128 | <0.063 | <0.063 | <0.063 | 16 | |

[a]In the combination assay, the 25-azacholesterol concentration was assayed at either 128 AC(128), at 32 AC(32) or at 8 AC(8) mg/ml; and terbinafine T was titrated from 128 ug/ml to 0.063 ug/ml.

From the test results, the known dosage ranges of the various fungistatic compounds, and the concentration of the 25-azasterol compound which is not inhibitory to the growth of fungi, a synergistic antifungal or fungicidal composition may be achieved for controlling mycotic infections, the fungistatic or fungicidal effect being dependent primarily on the antifungal agent. Potentiation may be obtained when the azasterol compound is employed in an amount of from about ¼ to ½ or even 1/30 th of the amount of the non-steroidal antifungal agent. For the combinations to produce a fungicidal effect, the amount of the 25-azasterol compound may be increased over that needed to produce the synergistic antifungal effect. However, it is to be kept in mind that since the antifungal property resides primarily in the non-steroidal entity and it is oftentimes the desire to decrease the amount of this non-steroidal entity to take advantage of its antifungal property while reducing undesired side reactions, the actual amount of the steroidal agent is not necessarily of primary consideration and the desired useful potentiating effect may be obtained with an amount of the steroidal entity in weight excess rather than in a small fraction by weight. The actual ratio of the steriodal potentiating agent to the antifungal agent will be dependent not only on the non-steroidal fungistat but on the particular organism being controlled. Thus, the actual ratio is not critical. The present invention contemplates use of a subfungistatic amount of the fungistat selected together with an amount of azasterol compound which is non-inhibitory to fungal growth. For therapeutic control of mycotic infections from about 1.5 to about 5.0 mg/kg of body weight of the non-steroidal antifungal agent and similarly an amount of 1.5 to 5.0 mg/kg of body weight of the azasterol compound may be administered per day while considering patient's health, weight, age and other factors which influence response to a drug as well as the particular drug to be employed. The amounts when expressed as doses suitable for use in human subjects are in the range of from about 100 to about 400 mg of the non-steroidal antifungal agent and 50 to 400 mg of the azasterol compound given BID by oral or parenteral route.

The outstanding properties are most effectively utilized when the azasterol compound and a non-steroidal antifungal agent are formulated into novel pharmaceutical compositions with a pharmaceutically acceptable carrier according to conventional pharmaceutical compounding techniques.

The synergistic combination may be formulated for injection and may be presented in unit dosage form in ampoules or in multidose containers, if necessary with an added preservative. The compositions may also take such forms as suspensions, solutions or emulsions in oily or aqueous vehicles, and may contain formulating agents such as suspending, stabilizing and/or dispersing agents. Alternatively, the active ingredients may be in powder form for reconstituting with a suitable vehicle prior to parenteral or oral administration.

For parenteral applications the drugs are preferably formulated in conventional parenteral solutions such as 0.85 percent sodium chloride or 5 percent dextrose in water, with formulation aids such as desoxycholate or other pharmaceutically acceptable compositions.

The compounds also may be prepared in tablet or capsule form as well as in liquid form for oral administration. In preparing the compositions in oral dosage form, the component drugs are intimately admixed with any of the usual pharmaceutical media, including for liquid preparations, liquid carriers such as water, glycols, oils, alcohols, and the like, and for solid preparations such as capsules and tablets, solid carriers such as starches, sugars, kaolin, ethyl cellulose, generally with lubricant such as calcium sterate, together with binders, disintegrating agents and the like. Because of their ease in administration, tablets and capsules represent the most advantageous oral dosage form.

It is especially advantageous to formulate the compositions in unit dosage form for ease of administration and uniformity of dosage. Compositions in unit dosage form constitutes as aspect of the present invention. The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 400 milligrams of the non-steroidal antifungal agent and from about 50 to 400 milligrams of the axasterol compound, preferably about 100 to 200 milligrams of the nonesteroidal antifungal agent and 100 to 200 milligrams of the azasterol compound.

The following examples illustrate novel compositions but are not to be construed as limiting:

EXAMPLE A 1000 compressed tablets each containing 100 milligrams of N,N-dimethyl-3β-acetoxy 5,22(3)-choladiene-24-amine (Compound Ic) and 200 milligrams of lovastatin are prepared from the following formulation:

| | Grams |
|---|---|
| Compound Ic | 100 |
| Lovastatin | 200 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 100 milligrams of 25-azacholesterol and 200 milligrams of terbinafine are prepared from the following formulation:

|  | Grams |
|---|---|
| 25-Azacholesterol | 150 |
| Terbinafine | 200 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 1000 hard gelatin capsules, each containing 210 milligrams of N,N-dimethyl-3β-hydroxy-5,22(Z)-choladiene-24-amine (Compound Ib) and 290 milligrams of lovastatin are made by blending the following composition and used to fill two-piece hard gelatin capsules.

|  | Grams |
|---|---|
| Compound Ib | 210 |
| Lovastatin | 290 |
| Starch | 250 |
| Lactose | 750 |
| Talc | 250 |
| Calcium Stearate | 10 |

EXAMPLE D

In a similar manner 1000 gelatin capsules each containing 210 milligrams of 25-aza-22-oxacholesterol (Compound Id) and 290 milligrams of 1-methyl-2-nonyl-5-(phenylemthyl)-3-pyrrolidinol (Compound C).

|  | Grams |
|---|---|
| Compound Id | 210 |
| Compound C | 290 |
| Starch | 250 |
| Lactose | 750 |
| Talc | 250 |
| Calcium stearate | 10 |

EXAMPLE E 1000 compressed tablets each containing 200 milligrams of 25-azacholesterol and 300 milligrams of 5-(1-hydroxy-2,4,6-heptatriynyl)-2-oxo-1,3-dioxalane-4-heptanoic acid carbonate (Compound B) are prepared in a manner similar to that described in Example A from the following formulation:

|  | Grams |
|---|---|
| 25-Azacholesterol | 200 |
| Compound B | 300 |
| Starch | 750 |
| Dibasic calcium phosphate hydrous | 5000 |
| Calcium stearate | 2.5 |

EXAMPLE F 1000 hard gelatin capsules, each containing 210 milligrams of 25-azacholesterol and 290 milligrams of 11-(3-(hydroxymethyl)-4-oxo-2-oxetanyl)-7-methyl-2,4-undecadienoic acid (Compound A) are prepared in a manner similar to that described in Example B from the following formulation:

|  | Grams |
|---|---|
| 25-Azacholesterol | 200 |
| Compound A | 290 |
| Starch | 250 |
| Lactose | 750 |
| Talc | 250 |
| Calcium stearate | 10 |

What is claimed is:

1. A method for potentiating the antifungal properties of an antifunga agent comprising coadministering a 25-azasterol compound with a non-steroidal antifungal agent.

2. A method according to claim 1 wherein the 25-azasterol compound is a compound represented by the formula

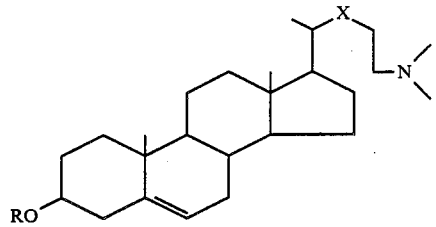

wherein R is hydrogen or lower acyl, X is CH, $CH_2$ or O; and the ---------- on the side chain indicates that the bond may be a single or a double bond provided that when X is O, or $CH_2$, it is a single bond.

3. A method according to claim 1 wherein the 25-azasterol compound is 17β-[[3-(dimethylamino)-propyl]methylamino]androst-en-3β-ol (25-azacholesterol).

4. A method according to claim 1 wherein the non-steroidal antifungal agent is employed in a subfungistatic amount and the 25-azasterol compound is employed in an amount not inhibitory to fungal growth.

5. A method according to claim 1 in which the antifungal compound is a lanosterol synthesis inhibitor.

6. A method according to claim 5 in which the antifungal compound is a mevalonic acid synthesis inhibitor.

7. A method according to claim 6 in which the mevalonic acid synthesis inhibitor is a HMG-CoA synthase inhibitor.

8. A method according to claim 7 in which the HMG-CoA synthase inhibitor is 11-(3-(hydroxymethyl)-4-oxo-2-oxethanyl)-7-methyl-2,4-undecadienoic acid.

9. A method according to claim 7 in which the mevalonic acid synthesis inhibitor is a β-ketothiolase inhibitor.

10. A method according to claim 9 in which the β-ketothiolase inhibitor is 5-(1-hydroxy-2,4,6-heptatriynyl)-2-oxo-1,3-dioxolane-4-heptanoic acid.

11. A method according to claim 7 in which the mevalonic acid synthesis inhibitor is a HMG-CoA reductase inhibitor.

12. A method according to claim 11 in which the HMG-CoA reductase inhibitor is 1,2,3,7,8,8a-hexahydro-3,7-dimethyl-8-[2-(tetrahydro-4-hydroxy-6-oxo-2H-pyran-2-yl)ethyl]-1-naphthalenyl-2-methylbutanoate (lovastatin).

13. A method for treating mycotic infections comprising administering subjects with an antifungally effective amount of a composition comprising a subfungistatic amount of a non-steroidal antifungal compound and a 25-azasterol compound in an amount not inhibitory to fungal growth.

14. A method according to claim 13 wherein the 25-azasterol compound is 25-azacholesterol.

15. A method according to claim 13 wherein the non-steroidal antifungal compound is administered in a daily dose in an amount of from about 1.5 to 5.0 mg/kg of body weight and the 25-azasterol compound is employed in an amount which is from about 1.5 to 5.0 mg/kg of body weight.

16. An improved antifungal composition comprising:
(1) an azasterol compound represented by the formula

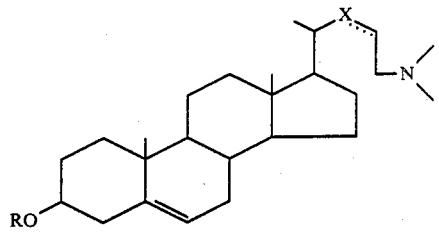

wherein r is hydrogen or lower acyl, X is CH, $CH_2$ or O; and the ............. on the side chain indicates that the bond may be a single or a double bond provided that when X is O, or $CH_2$, it is a single bond; and
(2) a non-steroidal antifungal compound in admixture with a pharmaceutically acceptable carrier.

17. A composition according to claim 16 wherein the azasterol compound is employed in an amount of from about 50 to 200 milligrams and the non-steroidal antifungal compound is employed in an amount of from about 100 to 400 milligrams.

18. A composition according to claim 17 wherein the 25-azasterol compound is 25-azacholesterol.

19. A composition according to claim 17 wherein the 25-azasterol compound is (3β,22Z)-24(dimethylamino)-chola-5,22-dien-3-ol.

20. A composition according to claim 17 wherein the 25-azasterol compound is 25-aza-22-oxacholesterol.

* * * * *